United States Patent
von Rundstedt et al.

(10) Patent No.: US 10,918,033 B2
(45) Date of Patent: Feb. 16, 2021

(54) DEVICE AND METHOD FOR PROPAGATING PLANTS

(71) Applicant: ROBOTEC PTC GmbH, Bremen (DE)

(72) Inventors: Friederike von Rundstedt, Bremen (DE); Stephan von Rundstedt, Bremen (DE)

(73) Assignee: RoBoTec PTC GmbH, Bremen (DE)

( * ) Notice: Subject to any disclaimer, the term of this patent is extended or adjusted under 35 U.S.C. 154(b) by 114 days.

(21) Appl. No.: 16/321,507

(22) PCT Filed: Jul. 31, 2017

(86) PCT No.: PCT/EP2017/000922
§ 371 (c)(1),
(2) Date: Jan. 29, 2019

(87) PCT Pub. No.: WO2018/024369
PCT Pub. Date: Feb. 8, 2018

(65) Prior Publication Data
US 2019/0183078 A1    Jun. 20, 2019

(30) Foreign Application Priority Data

Aug. 3, 2016 (DE) .......... 10 2016 009 352
Sep. 5, 2016 (DE) .......... 10 2016 010 618

(51) Int. Cl.
*A01H 4/00* (2006.01)
*A01G 9/08* (2006.01)

(52) U.S. Cl.
CPC ............. *A01H 4/005* (2013.01); *A01G 9/086* (2013.01); *A01H 4/00* (2013.01); *A01H 4/001* (2013.01); *A01H 4/003* (2013.01)

(58) Field of Classification Search
CPC . A01G 9/02; A01G 9/086; A01H 4/00; A01H 4/001; A01H 4/003; A01H 4/005
See application file for complete search history.

(56) References Cited

U.S. PATENT DOCUMENTS 5,370,713 A * 12/1994 Hanseler ................ A01H 4/001
47/1.01 R

FOREIGN PATENT DOCUMENTS

WO          9203913 A1    3/1992

OTHER PUBLICATIONS

WIPO, International Search Report (on parent application), dated Nov. 22, 2017, 2 pages.

* cited by examiner

*Primary Examiner* — Kent L Bell
(74) *Attorney, Agent, or Firm* — Laurence P. Colton; Smith Tempel Blaha LLC

(57) ABSTRACT

A method and a device for propagating plants, by way of which the risk of contamination can be minimized and the costs of the production of plants can be reduced. This is achieved in that the plants to be propagated are automatically grasped by a first gripper and separated, the individual plants, hanging on the first gripper, are systematically cut into multiple clones and the individual clones are automatically transported away by a second gripper for further processing.

20 Claims, 3 Drawing Sheets

DEVICE AND METHOD FOR PROPAGATING PLANTS

CROSS REFERENCE TO RELATED APPLICATIONS

This application is the US PCT National Phase of International Application No. PCT/EP2017/000922 having an International Filing Date of 31 Jul. 2017, which claims priority on German Patent Application No. 10 2016 009 352.8 having a filing date of 3 Aug. 2016 and German Patent application No. 10 2016 010 618.2 having a filing date of 5 Sep. 2016.

BACKGROUND OF THE INVENTION

Technical Field

The invention relates to a method for propagating plants, wherein the plants to be propagated are firstly automatically grasped by a first gripper and separated, the individual plants, hanging on the first gripper, are systematically cut into a plurality of clones, and the individual clones are automatically transported away by a second gripper for further processing. Furthermore, the invention relates to a device for propagating plants having at least one first gripper for the systematic grasping and separation of a plant to be propagated, having at least one apparatus for automatically cutting the plant into multiple clones, having at least one second gripper for automatically transporting away individual clones, and a room, in which the grippers and the at least one apparatus for cutting are arranged.

Prior Art

Ornamental and useful plants are increasingly needed for industrial applications. In this case, defined properties of these plants, such as the visual appearance, a high oil content, specific resistances, or the like are important in particular. To meet the increased demand, seedlings of these plants are produced in high piece counts in laboratories under sterile conditions as clones via tissue cultures. This in vitro propagation of the plants, in particular the propagation of "tailor-made" plant seedlings, is performed manually. This means that the individual plant seedlings have to be picked up by a person and trimmed appropriately for the propagation. The clones of the plants thus produced are then supplied to a culture medium, so that the clones grow further and propagate by germination.

This in vitro method is very labor-intensive and thus entails very high costs. However, since propagating plants having defined properties is one of the key industries of biotechnology, the costs have to be reduced dramatically for the expansion of this technology. Moreover, a running risk of contamination with bacteria exists due to the manual processing on open workbenches, which can result in the loss of the entire production.

BRIEF SUMMARY OF THE INVENTION

The invention is therefore based on the object of providing a method and a device for propagating plants, by way of which the costs of the production of plants can be reduced.

One solution to this object is a method in which the plants to be propagated are automatically grasped and separated by a first gripper, the individual plants, hanging on the first gripper, are systematically cut into a plurality of clones, and the individual clones are automatically transported away by a second gripper for further processing. The use of costly personnel can be dispensed with nearly completely due to this full automation of the method for propagating plants. It is therefore possible to reduce the cost for the production of plants massively by this automation of the method. In addition, the risk of contamination is minimized by this method.

This method is applicable to both useful and also ornamental plants. In particular, it can be provided according to the invention that the plants to be propagated are introduced in an initially closed, in particular marked container into a closed, sterile room and the containers are automatically opened in the room, in particular by at least one suction cup. To prevent bacteria, which can have negative effects on the growth of the plants, from propagating to further plants, the entire method for propagating plants takes place in a closed and/or sterile room. This cell-like room can also be, for example, a clean room. To keep the atmosphere in the closed room as sterile as possible, the plant seedlings or the plants are firstly introduced in a closed container through, for example, an airlock into the room. This container is opened by an apparatus for opening the container, such as, for example, a suction cup. The cover of the container fastened on the suction cups can then be disposed of. Items of information which are possibly positioned on the cover and describe the content of the container can be automatically input and stored, for example, and are used in the further method as an identification of the individual seedlings. The open container is then transported further by a corresponding device.

A further advantageous exemplary embodiment of the present invention can provide that the open container is supplied to a first image recognition unit and suitable positions are determined by the image recognition unit, at which the individual plants are grasped in succession by the first gripper and removed from the container. The individual plants or plant seedlings located in the container form an extremely nonuniform, i.e., inhomogeneous topography of leaves, stems, or the like. In order that the plants can be selectively grasped by the first gripper and it does not grasp at empty space or even grasp at a position at which the cut is to be carried out later, firstly the overall topography of the plants, i.e., the entirety of the leaves which protrude upward in the container, is recorded and processed by a control unit. This control unit then determines via image recognition which position on the plants is particularly well suited for the plants to be picked up by the gripper. When such a position has been determined, the gripper, which is similar to tweezers in particular, is guided by a robot arm to the corresponding position and the plant seedling is taken from the container. In this case, the individual containers are fixed by a partial vacuum on the bottom. The plant thus grasped is then supplied by the robot arm to a further station for the propagation of the plants.

Furthermore, it can be provided according to the invention that cutting lines on the plant hanging on the first gripper are determined by a second image recognition unit, along which cutting lines the plant is automatically cut by a blade, a laser beam, a waterjet, or a plasma beam into clones of the plant. In this case, the cutting line through the plant is determined by the image recognition unit corresponding to the predetermined specifications. Criteria are already defined and transmitted to the control unit of the image recognition unit before carrying out the propagation process, according to which criteria the cut has to be carried out so that the plant can grow further without problems after the cutting. The cutting of the plant by means of laser beam represents a contactless and accurate method for dividing a plant.

It can be provided according to the invention that the clones are transported, preferably on a conveyor belt, to a third image recognition unit, positions are determined, at which the individual clones are grasped by a second gripper and placed in a container, preferably according to a programmed setting pattern in the container. The clones cut off from the plant held on the first gripper fall because of gravity onto the conveyor belt, which is arranged precisely below the apparatus for cutting the plant. Propelled by this conveyor belt, the clones are then guided into a region which is associated with the third image recognition unit. A position is determined by this image recognition unit on the individual clones, which appears to be particularly suitable in order to grasp the clone by way of a second gripper and place it in a prepared container. During the placement, the gripper can follow a predetermined matrix, so that the plants are positioned in the highest possible density in the container, without mutually disturbing one another.

A further exemplary embodiment of the present invention can provide that the container containing a nutrient medium is opened before the clones are accommodated in the sterile room and is closed again after the clones are accommodated in the room, before the container is transported out of the room. Precisely like the containers in which the plants were supplied to the room, the containers in which the clones are taken away are also fixed by a suction force acting on the bottom of the containers. The containers are supplied to the room having an identified cover. The identification of the cover contains items of information about the culture medium. After the cover is removed by, for example, a suction cup and the individual clones are added to the container, the container is closed again using the same cover. Upon removal of the freshly populated containers, they are provided with items of information about the accommodated clones. In this manner, for example, a cross-contamination of various containers can be avoided. In addition, a continuous documentation of the containers and the clones exists over the entire process of the propagation. The containers containing the culture medium are supplied via a slide or a conveyor belt to the room. Similarly, the containers filled with the clones can leave the room again via an airlock, for example.

The invention can furthermore provide that the room and/or the grippers are regularly sterilized, in particular after the passage of a plant batch to be propagated. This sterilization is used for killing bacteria, which have arrived in the room due to a contaminated plant batch, for example. A UV irradiation by corresponding lighting means arranged in the room, by heating, or by gassing the room using hydrogen peroxide, for example, is used for the decontamination, for example.

A device for achieving the object mentioned at the outset is a device for propagating plants having at least one first gripper for the systematic grasping and separation of a plant to be propagated, having at least one apparatus for automatically cutting the plant into multiple clones, having at least one second gripper for automatically transporting away individual clones, and a room, in which the grippers and the at least one apparatus for cutting are arranged. A device is accordingly provided having at least one first gripper for selectively grasping and separating a plant to be propagated, and having at least one apparatus for automatically trimming the plant into multiple clones, and having at least one second gripper for automatically transporting away individual clones, wherein the grippers and the at least one apparatus for cutting are arranged in a room. A manual action of an operator is no longer necessary due to this automation of the device for propagating the plants. The entire in vitro propagation of the plants is carried out fully automatically by the claimed device. The removal of the plant seedlings from a container, the separation of the plants, the cloning, and the supply of the clones into a nutrient medium for the further growth process are all automatically controlled by a control system. The production costs of industrially produced plants may thus be reduced.

The invention can preferably provide that the room is a sterile clean room having multiple accesses, in particular airlocks, for the inward and outward transfer of containers having the plants and clones to be propagated, wherein at least two conveyor elements, preferably turntables, for the containers are associated with the room, in particular the accesses of the room, using which conveyor elements the containers are automatically movable into predetermined positions. Containers which arrive in the room for propagating the plants through the airlocks are accommodated directly by receptacles in the turntables and are transported away therefrom by a rotating movement of the conveyor elements. The containers having the plants are guided along the various stations for propagating plants and transferred outward out of the room as empty containers at the end of the rotation through an airlock by the rotation of the conveyor elements or the turntables.

The room can have a ventilation system on an upper side, by which system a sterile atmosphere can be obtained in the room. The room may be sterilized after every propagation process of a specific plant by additional sterilizers such as UV lamps, gassing systems, or the like. In addition, the room can have sensors, for example, using which the sterility of the room can be proven and/or documented. A container filled with nutrient solution can also be used for this purpose, for example, which container can be checked for growth at regular intervals.

In particular, it can furthermore be provided that at least one apparatus, in particular at least one suction cup, for automatically opening and/or closing the containers is associated with the conveyor elements. During the introduction of the containers into the room, the covers of the containers are removed by a suction cup, while the container body itself is fixed on a bottom of the conveyor element by a corresponding counter force, which can also be generated by a suction cup, for example. The suction cup is designed to be movable in such a way that the cover can be disposed of in a disposal shaft. A suction cup for removing the cover is associated with containers which are used for accommodating the clones. This removed cover is then transferred to a further suction cup, which in turn closes the cover after filling the container with the clones.

A further advantageous exemplary embodiment of the present invention can provide that at least one conveyor element, preferably both conveyor elements and/or a conveyor belt, is/are each associated with an image recognition unit for determining a suitable position, at which a plant and/or a clone can be automatically grasped by the first and/or second gripper, in particular by tweezers arranged on a multiaxis robot arm. This image recognition unit can be, for example, a CCD camera, which is coupled to a control system. The recorded shapes are analyzed and compared to a data system by this control system. Preferred positions on the plants which are particularly well suited for grasping the plants by the gripper can be determined by this comparison. The controller for the image recognition units, for the grippers, and for the robot arms is located in a base element of the device. The robot arms holding the gripper are designed in such a way that they can move in all spatial directions and thus a transfer of the plants from one position into another position is possible. The gripper essentially consists of tweezers, which can be systematically opened and closed by a positioning motor. Two widened areas are located at the tips of the tweezers, to make picking up the plants particularly gentle.

It can be provided according to the invention that the apparatus for automatically cutting the plant is a laser, a plasma generator, a blade, pincers, or a water cutter, with which a second image recognition unit is associated for determining suitable cutting lines, wherein a conveyor belt for conveying away the clones is associated with the apparatus for automatically cutting the plant. This second image recognition unit is also preferably a CCD camera, which is connected to a control unit. The laser, which can be a CO2 laser, for example, is mounted so it is movable in such a way that it can follow the cutting lines computed by the image recognition unit exactly and can thus cut multiple clones out of the plant.

BRIEF DESCRIPTION OF THE DRAWINGS

One preferred exemplary embodiment of the invention will be described in greater detail hereafter on the basis of the drawing. In the figures.

DETAILED DESCRIPTION OF PREFERRED EMBODIMENTS

Figure 1:
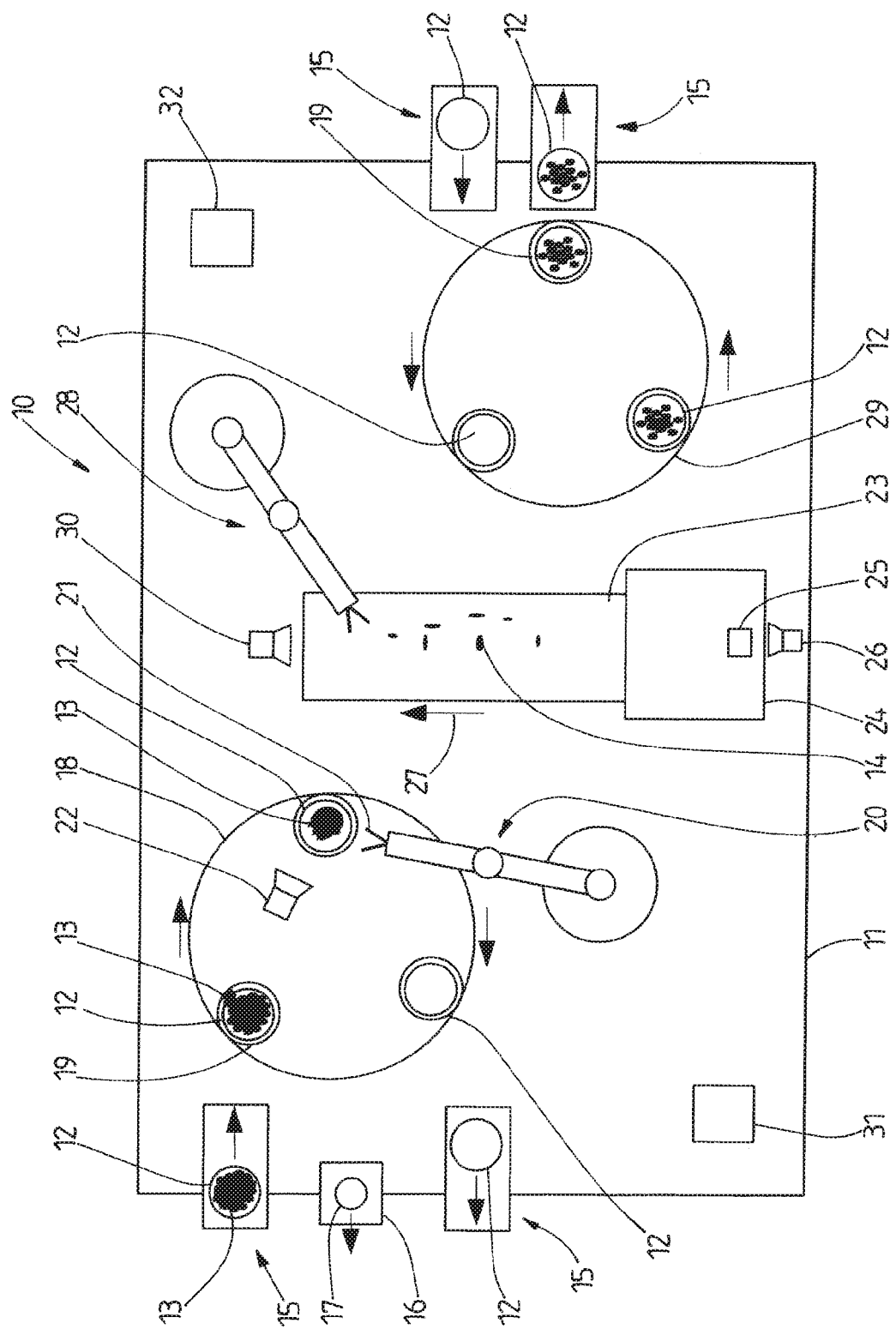
FIG. 1 shows a schematic illustration of a device in a first method step.

The device 10 for propagating plants, which is shown very schematically in FIG. 1, is essentially housed in a closed room 11. A sterile atmosphere is located in this room 11, at least during the method according to the invention for propagating plants 13. A ventilation system (not shown) is located above this room 11 for the climate control and/or venting of the room 11. The electronic controller (not shown) of the device 10 is located below the room 11.

Airlock-type accesses 15 are associated with the room 11 for supplying containers 11, in which both the plants 13 to be propagated and also the clones 14 thereof can be transported. These accesses 15 are also used for the outward transfer of the containers 12, which are empty or filled with clones, from the room 11. Moreover, a further airlock-type access 16 is associated with the room 11, for the outward transfer of covers 17 of the containers 12 out of the room 11.

The airlock-type accesses 15, 16 are particularly suitable for introducing the containers 12 into the room 11 or removing them therefrom fully automatically, without an excessive amount of air exchange occurring with the surroundings of the device 10. This is necessary in particular for maintaining the sterile atmosphere in the room 11.

Two turntable-like conveyor elements 18, 29 are arranged in the exemplary embodiment shown in FIG. 1 for the transportation of the containers 12 into the device 10 or into the room 11. These turntable-like conveyor elements 18, 29 may be rotated clockwise about a vertical axis and each have three receptacles 19 for accommodating the containers 12 here. These receptacles 19 have a suction cup (not shown), using which a container 12, which is located in the receptacle 19, can be fixed on the conveyor elements 18, 29.

Furthermore, movable suction cups (not shown) are associated with the conveyor elements 18, 29, using which the covers 17 of the initially closed containers 12 can be removed. The containers 12 can also be closed again with the covers 17 using these suction cups or using further suction cups.

A gripper 20 is associated with the conveyor element 18 for removing the plants 13 to be propagated from a container 12. This gripper 20 essentially consists of a multiaxis robot arm, with which automatically opening and closing tweezers 21 are associated at one end. Individual plants 13 or seedlings may be removed from the container 12, which is positioned in a receptacle 19 of the conveyor element 18, using this gripper 20. A first image recognition unit 22 is associated with the conveyor element 18 for the selective removal of a plant 13 by the gripper 20 or the tweezers 21. This image recognition unit 22 is preferably a CCD camera, which is connected to the electronic control system and recognizes specific shapes and accordingly transmits control signals to the gripper 20, so that it can grasp individual plants 13 with pinpoint accuracy.

A conveyor belt 23 is arranged between the conveyor elements 18, 29. An enclosure 24, in which a laser 25 is positioned, is located at one end of the conveyor belt 23. Plants can be cut using this laser 25, which can be a CO2 gas laser, for example. In order that the cutting of the plants runs with pinpoint accuracy and in a controlled manner, a second image recognition unit 26 is associated with the enclosure 24 and/or the laser 25. Precisely like the first image recognition unit 22, the second image recognition unit 26 is also connected to the electronic control unit. The image recognition unit 26 thus recognizes specific patterns, with which corresponding cutting lines can be associated. These items of information about the specific cutting lines are then transmitted to the laser 25, so that it can cut the individual plants 13 into clones 14.

The individual clones 14 can then be transported away in the direction 27 via the conveyor belt 23. A further gripper 28 is associated with an end of the conveyor belt 23 opposite to the laser 25. This gripper 28 is constructed similarly to the gripper 20. The individual clones 14 of the plant 13 may be picked up from the conveyor belt 23 using this gripper 28 and placed in sterile containers 12, which are located in the receptacles 19 of the conveyor element 29. In order that the gripper 28 can grasp the individual clones 14 from the conveyor belt 23, a third image recognition unit 30 is associated with the conveyor belt 23. This image recognition unit 30 is also connected to the electronic control system, precisely like the image recognition units 22 and 26, and determines preferred engagement points for the gripper 28 on the clones 14.

An apparatus 31, 32 for sterilizing is associated with each gripper 20, 28 for sterilizing the tweezers 21 of the grippers 20 and 28. For example, heat is applied to the tweezers 21, in order to possibly kill bacteria, in these apparatuses 31, 32. Furthermore, UV lamps can be located in the room 11, in order to irradiate the entire room 11 and thus sterilize it after the propagation of a plant batch.

Figure 2:
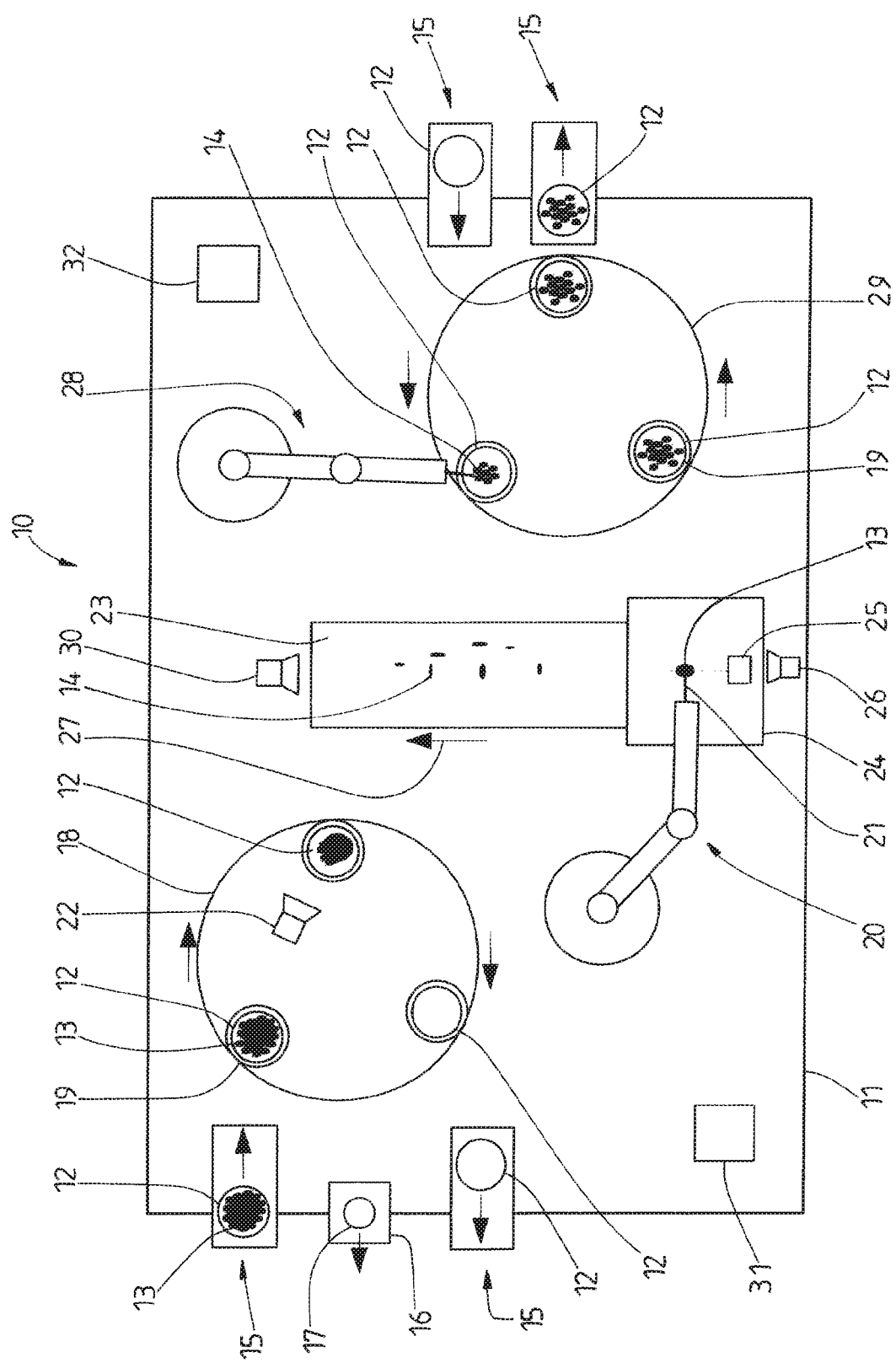
FIG. 2 shows a schematic illustration of the device in a second method step.

The method according to the invention for propagating plants will be described hereafter on the basis of FIGS. 1 to 3:

At the beginning of the method, a container 12, which has a plurality of the plants 13 to be propagated, is introduced through the access 15 into the room 11. The container 12 is automatically transferred there to a receptacle 19 of the conveyor element 18 and fixed by the suction cup in the receptacle 19. The cover 17 of the container 12 is then removed by a further movable suction cup and transferred out of the room 11 through the access 16.

The turntable-like conveyor element 18 having the container 12 is subsequently rotated clockwise. In the following position, the plants 13 in the containers 12 are recorded by the first image recognition unit 22 and a point and/or a leaf of a plant 13 are/is determined via the control unit, which point and/or leaf may be grasped particularly suitably by the gripper 20. When such a leaf has been determined, the gripper 20 approaches precisely this leaf in a fully automatic manner and separates the plant 13 (FIG. 1). The gripper 20 then guides the separated plant 13 into the enclosure 24.

In the enclosure 24, the plant 13 to be propagated is moved by the gripper 20 into a position which is registered by a second image recognition unit 26. This second image recognition unit 26 determines, together with the control system, multiple cutting lines, along which the plant 13 can be cut to produce clones 14 of the plant 13. When the cutting lines have been determined, the plant 13 is cut by the laser 25 into multiple clones 14 (FIG. 2). When the plant 13 cannot be cut further, it is permitted to fall onto the belt and the gripper 20 moves back to the container 12 in order to grasp a new plant 13. This procedure is continued until the container 12 no longer has plants 13. The empty container 12 is then transported away by the conveyor element 18 and transferred out of the room 11 through the access 15. At the same moment, a new container 12 is transferred inward through the access 15 into the room 11 and a container moves into the position in which the individual plants 13 can again be grasped by the gripper 20.

Figure 3:
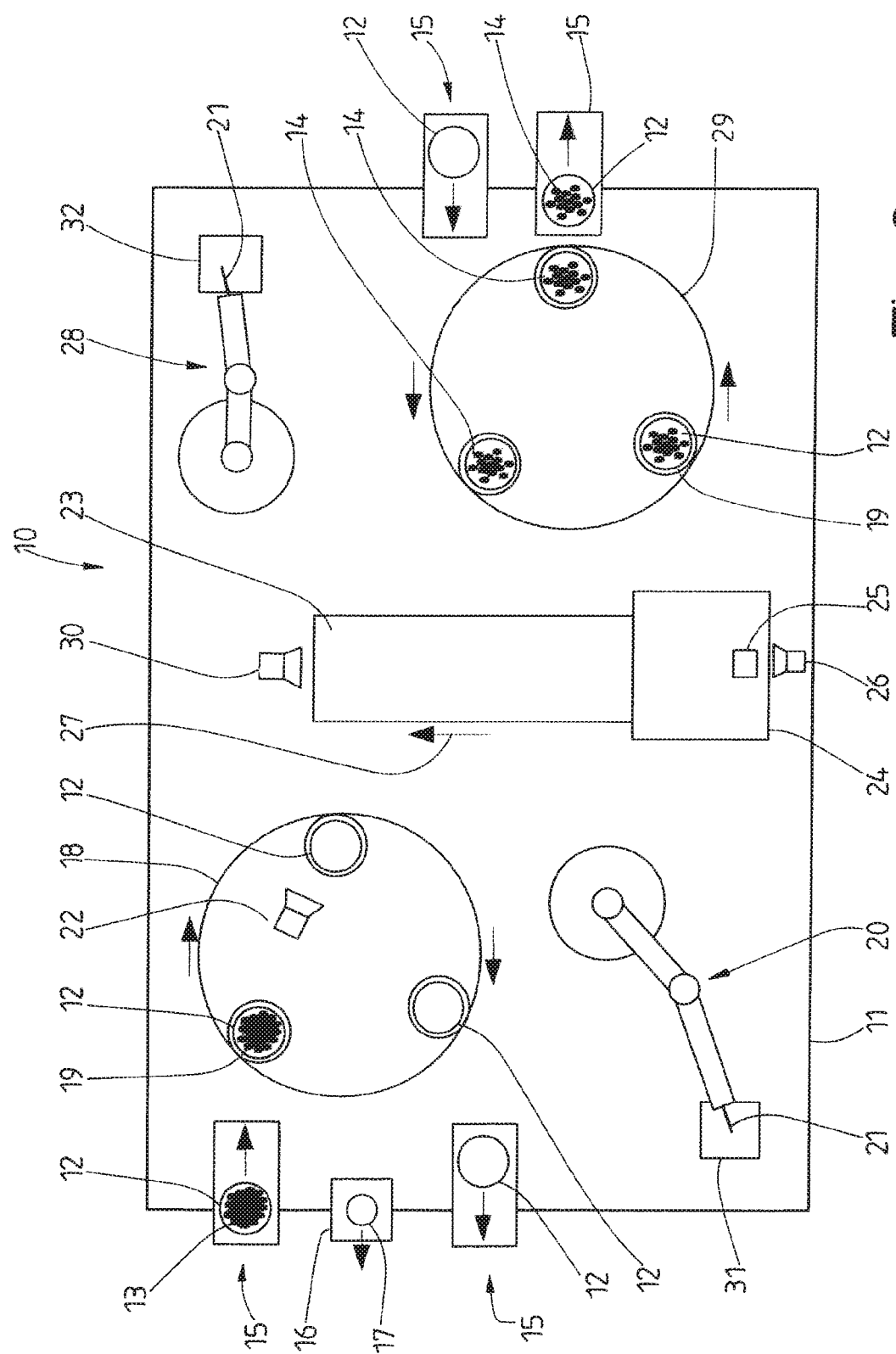
FIG. 3 shows a schematic illustration of the device according to a third method step.

The plants 13 cut by the laser 25 or the clones are transported away by the conveyor belt 23 in the direction 27 (FIG. 3). At the end of the conveyor belt 23, the clones are again recognized by the third image recognition unit 30 and a position is determined at which the individual clones 14 may be grasped particularly suitably by the second gripper 28. During this, the second conveyor element 29 was equipped with sterile containers 12. These sterile containers 12 are also transferred inward through accesses 15 into the room 11. These containers 12 are also initially fixed in the receptacles 19 by a suction cup. The cover 17 of a newly introduced container 12 is firstly removed by a movable suction cup and then transferred to a further suction cup, which recloses a container 12 filled with clones 14 using the same cover 17.

The conveyor element 29 rotates the containers 12 into a position in which the gripper 28 can press the individual clones 14 into the culture medium of the containers 12. The positioning of the individual clones 14 in the containers 12 is performed according to a pattern or a matrix. As soon as a container is filled and/or all spaces of a matrix are occupied, as just described, the container 12 is again provided with its cover 17 and transferred out of the room 11 through the access 15.

As soon as a batch of the plants 13 to be propagated has been processed, the tweezers 21 of the grippers 20 and 28 are guided to the apparatuses 31, 32 for sterilization. In this phase, the entire room 11 can also be sterilized by electromagnetic radiation and/or gassing. As soon as the sterilization is completed, a new batch of plants 13 can be propagated.

LIST OF REFERENCE SIGNS

10 Device
11 Room
12 Container
13 Plant
14 Clone
15 Access
16 Access
17 Cover
18 Conveyor element
19 Receptacle
20 Gripper
21 Tweezers
22 First image recognition unit
23 Conveyor belt
24 Enclosure
25 Laser
26 Second image recognition unit
27 Direction
28 Gripper
29 Conveyor element
30 Third image recognition unit
31 Apparatus
32 Apparatus

What is claimed is:

1. A method for propagating plants (13), comprising:
    the plants (13) to be propagated are firstly automatically grasped by a first gripper (20) and separated;
    cutting lines on the plant (13), hanging on the first gripper (20), are determined by a cutting line image recognition unit (26);
    the individual plants (13), hanging on the first gripper (20), are systematically cut into a plurality of clones (14) along the cutting lines, wherein the plant (13) is automatically cut along the cutting lines by a blade, a laser beam (25), a waterjet, or a plasma jet into the clones (14) of the plant (13); and
    the individual clones (14) are automatically transported away by a second gripper (28) for further processing.

2. The method for propagating plants (13) as claimed in claim 1, wherein in that the plants (13) to be propagated are introduced in an initially closed container (12) into a closed, sterile room (11) and the containers (12) are automatically opened in the room (11).

3. The method for propagating plants (13) as claimed in claim 2, wherein the open container (12) is supplied to a first gripper image recognition unit (22) and suitable positions are determined by the first gripper image recognition unit (22), at which suitable positions the individual plants (13) are successively grasped by the first gripper (20) and removed from the container (12).

4. The method for propagating plants (13) as claimed in claim 1, wherein the clones (14) are transported, preferably on a conveyor belt (23), to a second gripper image recognition unit (30), positions are determined by the second gripper image recognition unit (30), at which the individual clones (14) are grasped by the second gripper (28) and placed in a container (12).

5. The method for propagating plants (13) as claimed in claim 2, wherein the container (12) containing a nutrient solution is opened in the sterile room (11) before the accommodation of the clones (14) and is closed again in the room (11) after the accommodation of the clones (14), before the container (12) is transported away out of the room (11).

6. The method for propagating plants (13) as claimed in claim 2, wherein the room (11) and/or the grippers (20, 28) are sterilized regularly.

7. A device (10) for propagating plants (13) comprising:
- at least one first gripper (20) for the systematic grasping and separation of a plant (13) to be propagated;
- at least one apparatus for automatically cutting the plant (13) into multiple clones (14), wherein the at least one apparatus for automatically cutting the plant (13) is a laser (25), a plasma generator, a blade, or a water cutter;
- an image recognition unit (26), associated with the at least one apparatus for automatically cutting the plant (13), for determining suitable cutting lines;
- a conveyor belt (23), associated with the at least one apparatus for automatically cutting the plant (13), for conveying away the clones (14);
- at least one second gripper (28) for automatically transporting away individual clones (14) from the conveyor belt (23); and
- a room (11), in which the grippers (20, 28) and the at least one apparatus for automatically cutting the plant (13) are arranged.

8. The device (10) for propagating plants (13) as claimed in claim 7, wherein the room (11) is a sterile clean room having multiple accesses (15, 16) for the inward transfer and outward transfer of containers (12) having the plants (13) to be propagated and the clones (14), wherein at least two conveyor elements (18, 29) for the containers (12) are associated with the room (11), using which conveyor elements the containers (12) are automatically movable into predetermined positions.

9. The device (10) for propagating plants (13) as claimed in claim 8, further comprising at least one apparatus for automatically opening and/or closing the containers (12) associated with the conveyor elements (18, 29).

10. The device (10) for propagating plants (13) as claimed in claim 7, further comprising an image recognition unit (22, 30) associated in each case with at least one of the conveyor elements (18, 29) and/or a conveyor belt (23), for determining a suitable position, at which the plant (13) and/or the clone (14) can be automatically grasped by the first and/or the second gripper (20, 28).

11. The method for propagating plants (13) as claimed in claim 2, wherein the closed container (12) is marked.

12. The method for propagating plants (13) as claimed in claim 2, wherein the containers (12) are automatically opened by at least one suction cup.

13. The method for propagating plants (13) as claimed in claim 4, wherein the individual clones (14) are placed in the container (12) according to grid in the container (12).

14. The method for propagating plants (13) as claimed in claim 6, wherein the room (11) and/or the grippers (20, 28) are sterilized after the passage of the plant batch to be propagated.

15. The device (10) for propagating plants (13) as claimed in claim 8, wherein the accesses (15, 16) are airlocks.

16. The device (10) for propagating plants (13) as claimed in claim 8, wherein the at least two conveyor elements (18, 29) are turntables.

17. The device (10) for propagating plants (13) as claimed in claim 8, wherein the at least two conveyor elements (18, 29) are associated with the accesses (15, 16) of the room (11).

18. The device (10) for propagating plants (13) as claimed in claim 9, wherein the at least one apparatus for automatically opening and/or closing the containers (12) is at least one suction cup.

19. The device (10) for propagating plants (13) as claimed in claim 10, wherein the image recognition unit (22, 30) is associated with both of the conveyor elements (18, 29) and/or the conveyor belt (23).

20. The device (10) for propagating plants (13) as claimed in claim 10, wherein the plant (13) and/or the clone (14) is gripped by tweezers (21) arranged on a multiaxis robot arm of the second gripper (20, 28).

* * * * *